United States Patent
Spiridigliozzi et al.

(10) Patent No.: US 8,333,203 B2
(45) Date of Patent: Dec. 18, 2012

(54) CUSTOM FITTED INTRA-ORAL APPLIANCES

(75) Inventors: John Spiridigliozzi, San Mateo, CA (US); Amir Abolfathi, Woodside, CA (US); Emir Deljkich, Dublin, CA (US)

(73) Assignee: Sonitus Medical, Inc., San Mateo, CA (US)

(*) Notice: Subject to any disclaimer, the term of this patent is extended or adjusted under 35 U.S.C. 154(b) by 838 days.

(21) Appl. No.: 12/169,145

(22) Filed: Jul. 8, 2008

(65) Prior Publication Data

US 2010/0006111 A1  Jan. 14, 2010

(51) Int. Cl.
*A61C 5/14* (2006.01)

(52) U.S. Cl. ........ 128/862; 381/151; 381/322; 381/324; 381/326; 433/6

(58) Field of Classification Search .......... 433/6, 24–25, 433/229; 128/859, 860–861; 607/51, 56–57; 381/151, 190, 312, 315, 322, 324, 326, 328, 381/380
See application file for complete search history.

(56) References Cited

U.S. PATENT DOCUMENTS

| 4,920,984 | A | 5/1990 | Furumichi et al. |
| 5,082,007 | A | 1/1992 | Adell |
| 5,447,489 | A * | 9/1995 | Issalene et al. ............... 600/25 |
| 5,616,027 | A | 4/1997 | Jacobs et al. |
| 6,200,133 | B1 * | 3/2001 | Kittelsen ............... 433/6 |
| 6,333,269 | B2 | 12/2001 | Naito et al. |
| 6,371,758 | B1 * | 4/2002 | Kittelsen ............... 433/6 |
| 7,361,216 | B2 | 4/2008 | Kangas et al. |
| 2006/0207611 | A1 * | 9/2006 | Anonsen ............... 128/859 |
| 2007/0280491 | A1 * | 12/2007 | Abolfathi ............... 381/313 |
| 2008/0019542 | A1 * | 1/2008 | Menzel et al. ........... 381/151 |
| 2008/0070181 | A1 | 3/2008 | Abolfathi et al. |

FOREIGN PATENT DOCUMENTS
WO  WO 2010/005913  1/2010

* cited by examiner

*Primary Examiner* — Patricia Bianco
*Assistant Examiner* — Camtu Nguyen
(74) *Attorney, Agent, or Firm* — Levine Bagade Han LLP (57) ABSTRACT

Methods and apparatus for transmitting vibrations via an electronic and/or actuator assembly through a custom-fitted dental appliance are disclosed herein. The customized fitting is done by the user. The assembly may be attached, adhered, or otherwise embedded intra-orally on a tooth or oral tissue. The electronic and actuator assembly may receive incoming sounds either directly or through a receiver to process and amplify the signals and transmit the processed sounds via a vibrating actuator element coupled to a tooth or other bone structure, such as the maxillary, mandibular, or palatine bone structure.

19 Claims, 8 Drawing Sheets

FIG. 10

CUSTOM FITTED INTRA-ORAL APPLIANCES

BACKGROUND

The present invention relates to custom fitted intra-oral dental devices.

Mouthguards are typically made from plastics materials such as an ethylene vinyl acetate copolymer (EVA). Other devices such as dentoalveolar trays, carriers and splints may be made of EVA or other biocompatible plastic material. There are several categories of mouthguards: Mouthguards that are stock pre-molded products and made in a variety of sizes, home or self-moldable to suit the physical characteristics of the user, or custom molded by a dentist or other professional to suit the characteristics of the user. Regarding physical protection, stock mouthguards are typically the cheapest and least effective in use while the custom molded and shaped mouthguards are the most expensive and effective in their impact absorbent properties.

U.S. Pat. No. 4,920,984 relates to a mouthguard material that may be custom shaped or molded employing a teeth impression cast pressed against softened thermoplastic sheet material that increases in thickness from one end to the other.

Australian patent specification 633269 discloses a mouthguard made from an EVA copolymer having a softening point higher than the normal temperature of an oral cavity but lower than the highest temperature that the oral cavity can endure so that the user may adapt the mouthguard to fit the mouth by biting onto it after it has been heated. The shaping procedure may be repeated if the shape or configuration of the teeth should change.

U.S. Pat. No. 5,082,007 a gel or fluid capsule is contained between the upper and lower portions of a mouthguard, as shown in FIG. 15. The nature of this gel is not described and appears to serve a mechanical, that is, a shock absorbing function.

U.S. Pat. No. 5,616,027 discloses a hard, thin dental tray, suitable for many types of dental and at home procedures and uses. The patent uses ethylene vinyl acetate for an outer, non-impression forming tray that can be softened using boiling water. The thin inner tray is customizable to the same accuracy as more expensive custom trays created on a model, but at a fraction of the cost in time, professional expertise or equipment. The inner tray is principally made of a composition of polycaprolactone polymer with co-polymers and additives. The thin dental trays can be customized and molded in the home or outside of a dental office.

SUMMARY

In one aspect, an intraoral apparatus includes an actuatable transducer to generate sound through bone conduction; and a user-fabricated custom fit base to attach the actuatable transducer to one or more teeth or oral tissue.

Implementations of the above aspect may include one or more of the following. The user fabricated custom fit base can be a thermoplastic co-polymer such as ethylene vinyl acetate (EVA) or polyethylene material, among others. The user fabricated custom fit base can also be a hardenable material that is injected into the base and hardened. A relief valve can discharge the excess hardenable material. First and second chambers can be mounted to the sides of a tooth. An arm can link the first and second chambers. The arm can have a loop to provide tension on the tooth. In one embodiment, the arm is corrugated, jagged, round, or rectangular to provide better contact with the tooth to deliver sound energy. The chamber slidably cooperates with the arm to fit different tooth sizes and locations. One chamber can contact the tooth to deliver sound energy. A moveable dental contact point can be provided on the chamber to allow a user to adjust a contact position with a tooth. An electronic assembly disposed within or upon the base. The electronic assembly is encapsulated within a housing. The electronic assembly can include a power supply such as a battery in electrical communication with transducer. A processor can be in electrical communication with the transducer. A microphone can receive auditory signals and which is in electrical communication with the processor. A receiver can be in wireless communication with an externally located transmitter assembly.

In another aspect, a method of transmitting vibrations includes heating a base material and biting into the base material to form a custom-fit base; positioning an actuatable transducer on the base; mounting the base and the actuatable transducer on one or more teeth or oral tissue; and generating sound with the actuatable transducer.

In yet another aspect, a method of transmitting vibrations includes injecting a base material into the base and biting into the base material to form a custom-fit base; allowing the base material to harden; positioning an actuatable transducer on the base; mounting the base and the actuatable transducer on one or more teeth or oral tissue; and generating sound with the actuatable transducer.

DESCRIPTION

Figure 1:
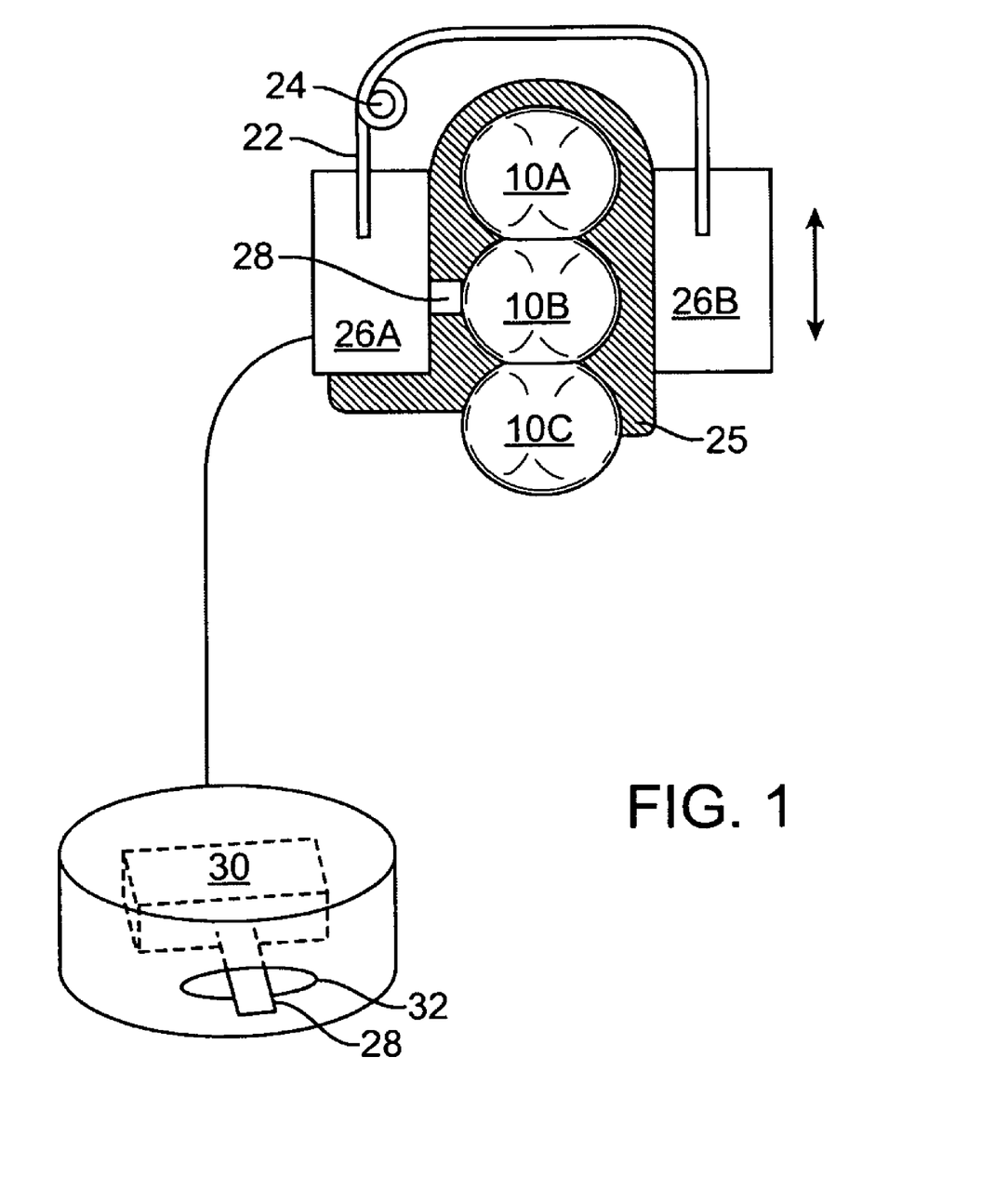
FIG. 1 illustrates one embodiment of a custom-fit device mounted on one or more teeth.

FIG. 1 shows an exemplary custom dental device that can be worn intra-orally by a patient over one or more teeth 10A, 10B and 10C. The device 8 has a custom fit layer 25 that can be formed or fabricated by a patient at home without requiring lab work. The custom fit layer 25 can be customized in the home to avoid the need to visit to a lab for taking a dental impression of the user's teeth and subsequently forming a custom appliance from the dental impression.

In one embodiment, the custom fit layer 25 can be a preformed tray made from a thermoplastic co-polymer, e.g., ethylene vinyl acetate or polyethylene material, which may be heated or boiled to activate the tray. Once activated, the user may bite into the tray to at least partially mold or conform the custom fit layer 25 to the user's dentition. The thermoplastic co-polymer ethylene vinyl-acetate can have a vinyl acetate proportion in the range of 27.2% to 28.8%, yielding a melt index of 22 to 28 decigrams/minute. A suitable product is Elvax 250 from DuPont.

Attached to the custom fit layer 25 are two chambers or assemblies 26A and 26B that house components associated with the dental device. The chambers or assemblies 26A-26B may be attached, adhered, or otherwise contact a tooth or oral tissue. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

The chambers or assemblies 26A-26B may be included or integrated after the custom fit layer 25 has been conformed. The assemblies 26A and 26B can be mechanically linked through an arm 22. The arm 22 can provide compressive forces that clip the assemblies 26A-26B to the one or more teeth in one embodiment. In another embodiment, the arm 22 has a loop 24 that enhances the compressive forces provided by the arm 22. The oral appliance may accordingly be created to fit, adhere, or be otherwise disposed upon a portion of the patient's dentition to maintain the electronics and transducer device against the patient's dentition securely and comfortably. One or more wires may be embedded in the arm 22 to support electrical communication between the two assemblies 26A-26B. For example, power cables can connect the battery in assembly 26B to the amplifier devices in assembly 26A.

Each of assemblies 26A-26B can be slidably adjusted to receive a longer or a shorter portion of the arm 22 in each assembly. When the arm 22 is buried deeply inside the assemblies 26A-26B, the arm 22 can encompass a small tooth. Alternatively, to accommodate a large tooth, the user can slide the assemblies 26A-26B away from the arm 22 to create more space to accommodate the large tooth.

In addition to the coarse adjustment discussed above, the user can also make fine grained adjustments on the tooth contact points, as detailed in the exploded view of the assembly 26A. An actuator or transducer device 30 may be attached, adhered, or otherwise embedded into one of the assemblies 26A-26B form a hearing aid assembly in one example, while the remaining assembly can be used to store power or other sources of energy for the custom fit appliance.

The actuator or transducer 30 is a mechanical device for moving or controlling a mechanism or system. The actuator or transducer can be a device, usually electrical, electronic, electromechanical, electromagnetic, photonic, or photovoltaic that converts one type of energy or physical attribute to another for various purposes including measurement or information transfer. The transducer can also act as a sensor, used to detect a parameter in one form and report it in another (usually an electrical or digital signal), and can also act as an audio loudspeaker, which converts electrical voltage variations representing music or speech, to mechanical cone vibration and hence vibrates air molecules creating acoustical energy.

The electronic and actuator device 30 may receive incoming sounds either directly or through a receiver to process and amplify the signals and transmit the processed sounds via a vibrating actuator element coupled to a tooth or other bone structure, such as the maxillary, mandibular, or palatine bone structure. The vibrating actuator element can be positioned on a tab 28 that contacts the tooth 10B. The inset shows that the assembly 26A has an elongated channel 32 that slidably engages the tab 28. To ensure an optimal contact with the tooth 10B, the user can hold the tab 32 and move the tab 32 along the elongated channel 32 to adjust the contact position for an optimal bone conduction.

In the variation of FIG. 1, oral appliance 8 may be fitted upon three molars 10A-10C for stability upon the patient's teeth, although in other variations, a single molar or tooth may be utilized. Alternatively, more than two molars may be utilized for the oral appliance 8 to be attached upon or over. Moreover, electronics and/or actuator assembly 30 is shown positioned upon a side surface of oral appliance 8 such that the assembly 30 is aligned along a buccal surface of the tooth 10B; however, other surfaces such as the lingual surface of the tooth 10B and other positions may also be utilized. The figures are illustrative of variations and are not intended to be limiting; accordingly, other configurations and shapes for oral appliance 8 are intended to be included herein.

In another variation, the removable oral appliance can be placed over an entire row of teeth in the manner of a mouthguard. In this variation, the appliance may be configured to cover an entire bottom row of teeth or alternatively an entire upper row of teeth. In additional variations, rather than covering the entire rows of teeth, a majority of the row of teeth may be instead be covered by appliance, for example.

In one variation of an oral appliance, a mouthguard or retainer may be inserted and removed easily from the user's mouth. Such a mouthguard or retainer may be used in sports where conventional mouthguards are worn; however, mouthguard or retainer having assembly 26A-26B integrated therein may be utilized by persons, hearing impaired or otherwise, who may simply hold the mouthguard or retainer between their teeth for receiving instructions remotely and communicating over a distance.

Generally, the volume of electronics and/or actuator assembly 30 may be minimized so as to be unobtrusive and as comfortable to the user when placed in the mouth. Although the size may be varied, a volume of assembly 30 may be less than 800 cubic millimeters. This volume is, of course, illustrative and not limiting as size and volume of assembly and may be varied accordingly between different users.

In one variation, with assemblies 26A-26B positioned upon the teeth, an extra-buccal transmitter assembly located outside the patient's mouth may be utilized to receive auditory signals for processing and transmission via a wireless signal to the electronics and/or actuator assembly 30 positioned within the patient's mouth, which may then process and transmit the processed auditory signals via vibratory conductance to the underlying tooth and consequently to the patient's inner ear.

Figure 2:
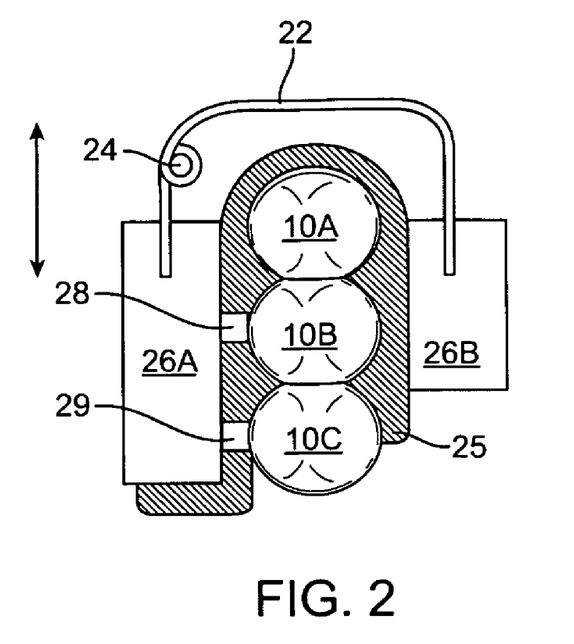
FIG. 2 shows a variation of FIG. 2 with two tooth contact points.

FIG. 2 shows an embodiment with two vibratory contact points 28-29 in the assembly 26A. The presence of the plurality of contact points enhances the bone conduction process to deliver sound to the user.

To fabricate the custom appliance, in one embodiment, the user heats a pot of water and then submerges his or her mouthpiece template into the hot water for 5 to 15 seconds. The mouthpiece template begins to wilt when heated. If the mouthpiece template is slightly too large for the user's arch, the user can keep the mouthpiece submerged for an extended duration and shrink the template. Next, the user places the mouthpiece into his or her mouth and presses the template against the teeth with his or her fingers and tongue. The template is allowed to cool and the mouthpiece template becomes perfectly molded to the user's teeth. The user can trim using a scissor, a knife, or any sharp instruments.

In another alternative, a mold may be generated from the print to then allow for thermal forming of the appliance directly upon the created mold. And yet in other variations, the three-dimensional image may be used to create an injection mold for creating the appliance.

In another embodiment, in lieu of the scaffold, a blank can be used in making a direct-formed mouthguard. The blank includes a material conformable to a contours of a user's intra-oral structures at a predetermined temperature range when the blank is subjected to bite pressure and an electronic and/or actuator assembly mounted on the material to couple to at least a portion of a patient's dentition. The actuator and/or electronics can be inserted into the material before or after the blank is subjected to bite pressure.

The blank provides a direct-formed thermoplastic mouthguard in which a stock plastic mouthguard is softened in hot water, placed in the users mouth and formed by the application of bite pressure, or a ready-made stock mouthguard used without the need for any fitting. The blank can be low in cost and thus can be sold at retail outlets.

In one implementation, the blank can be an inner layer of settable thermoplastic material conformable to the contours of the user's intra-oral structures at a predetermined temperature range when said blank is subjected to bite pressure; a core layer of rigid, force-transmitting thermoplastic material disposed adjacent to and coextensively with the inner layer and having a softening temperature higher than the pre-determined temperature range. The core layer is conformable to the general shape of the user's upper or lower row of teeth at said softening temperature to adjust the overall fit of the blank. An outer layer of settable, shock-absorbing thermoplastic material is disposed adjacent to and coextensively with the core layer. The outer layer is conformable to the contours of a user's intra-oral structures at a pre-determined temperature range when the blank is subjected to bite pressure. The electronics and/or the actuator can be placed inside the blank prior to use.

Figure 3A:
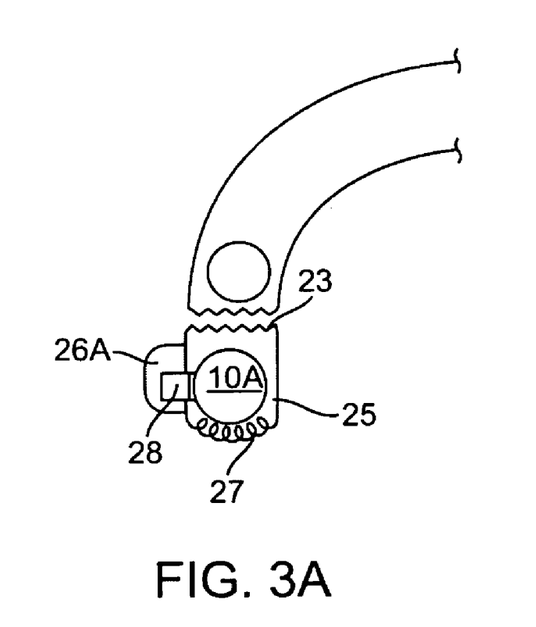
FIGS. 3A-3B shows two exemplary snap off dental appliance embodiments.
Figure 3B:
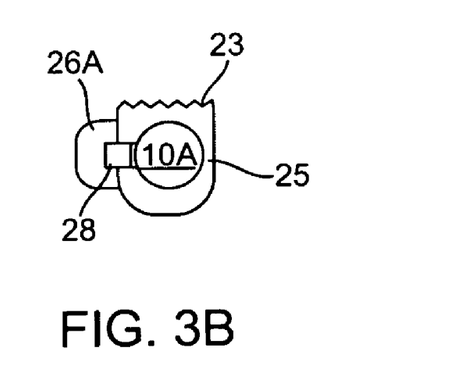

FIG. 3A and FIG. 3B show two embodiments of a custom appliance that can be formed by the user without the need for a dental lab. In this embodiment, a general arch template includes a thin edge or line 23 that is designed to snap off or break off from the rest of the template with minimal force. In FIG. 3A, after being snapped off, the custom fit layer 25 can be inserted over the molar tooth 10A. In this embodiment, the layer 25 leaves the back of the molar 10A open-ended. A wire 27 extends from one end of the layer 25 to the other end of the layer 25, and the wire provides a compressive force to secure the entire appliance on the molar tooth 10A. The assembly 26A then engages the tooth 10B with the contact point 28. FIG. 3B shows another version where the layer 25 completely surrounds the molar tooth 10A. In the embodiment of FIG. 3B, there is no wire 27.

Figure 4:
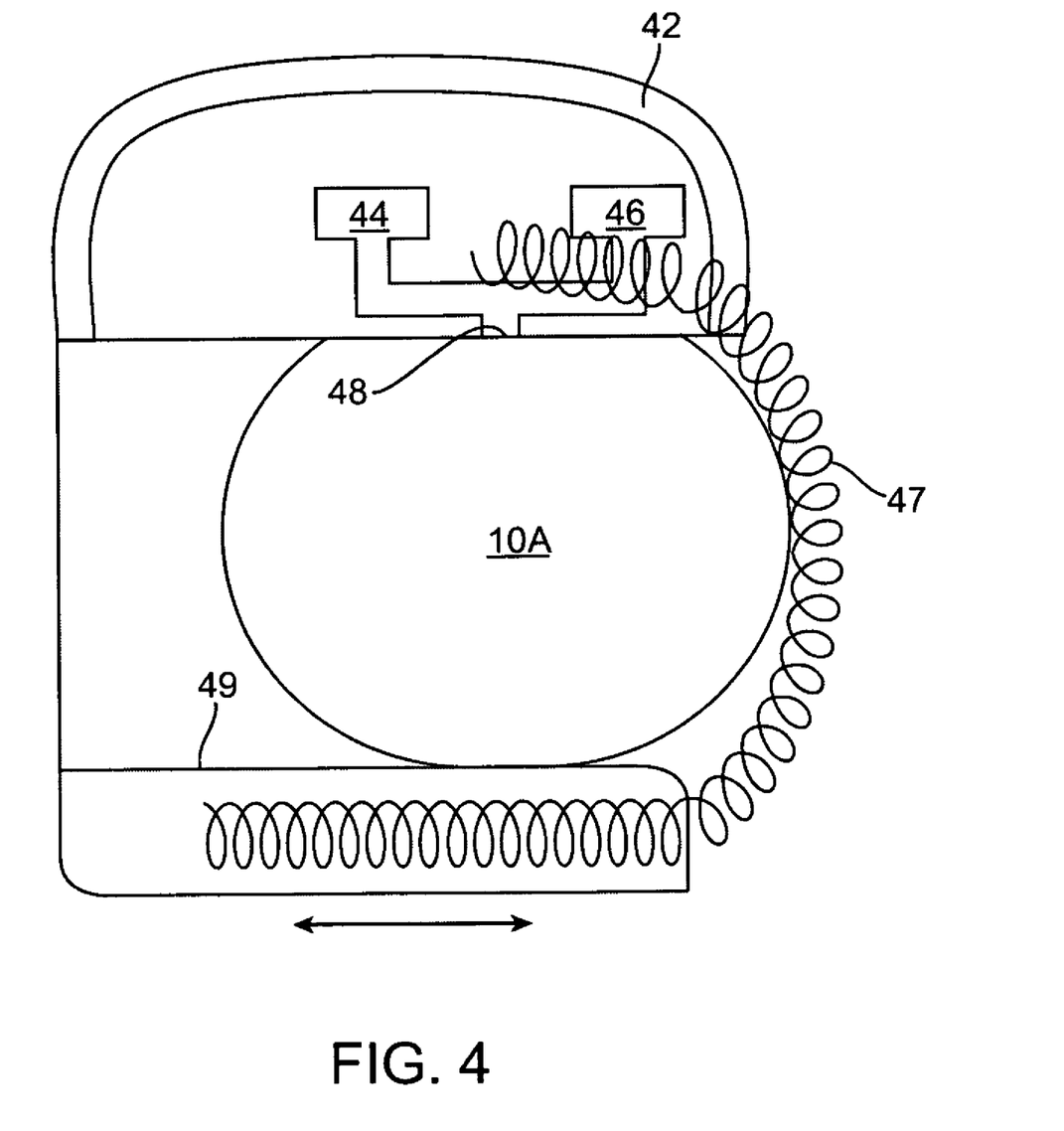
FIG. 4 shows in more detail the exemplary snap off custom dental appliance of FIG. 3A.

FIG. 4 shows in more detail, one exemplary appliance. In this embodiment, a custom fit layer has two side engagement portions: 42 and 49. Additionally, a spring or wire 47 provide flexibility in fitting the appliance over the tooth 10A and after seating the appliance on the tooth 10A, secure the appliance to the tooth 10A. Positioned on the portion 42 are two counterweights that are used for bone conduction transmission at contact point 48.

Figures 5A, 5B:
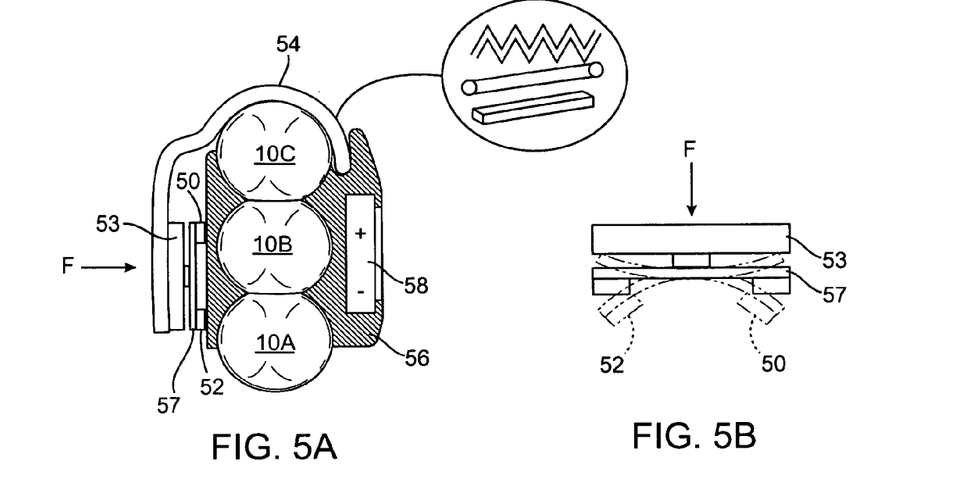
FIGS. 5A, 5B, 6A and 6B show exemplary cantilevered bone conduction dental appliance embodiments.

Referring now to FIGS. 5A, 5B, 6A and 6B, cantilevered bone conduction hearing appliances are shown. In FIG. 5A, a flexible, yet resilient conformal base 56 such as EVA provides a customized fit to attach the appliance to teeth 10A-10C. The conformal base 56 can be made using the "boil-and-bite" approach discussed above. However, since exposing energy storage devices such as lithium batteries to high temperature can degrade their function and can shorten their lifespan, the embodiment of FIG. 5 provides a battery slot 58 on one side of the conformal base 56. The battery is inserted just before use or after the high temperature shape boiling operation to ensure its integrity.

The conformal base 56 exposes one end of molar tooth 10C. The open end of molar 10C is in physical communication or contact with a rigid arm 54 that delivers mechanical impulses to the tooth 10C for bone conduction purposes. As shown in the inset, the arm 54 can be jagged, corrugated, cylindrical, or rectangular in shape. The arm 54 applies force on a mass 53 which is connected to a piezoelectric transducer 57. The transducer 57 makes mechanical contact with a tooth or a bone at contact points 50 and 52.

Figure 6A:
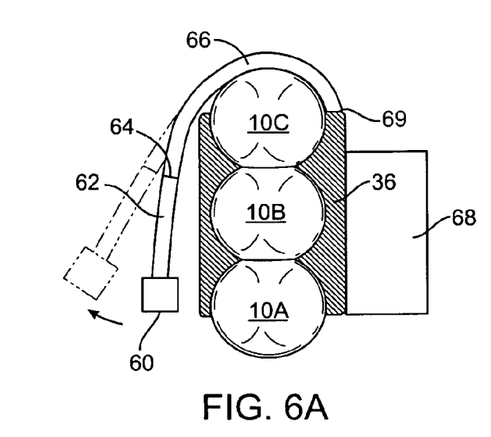
Figure 6B:
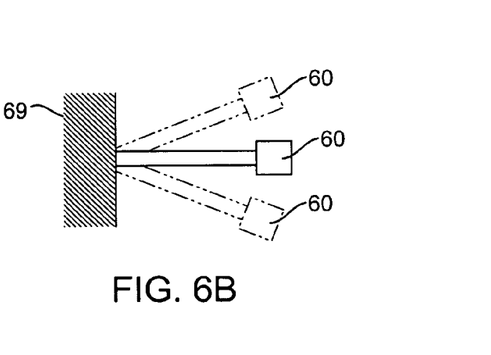

FIG. 5B shows in more detail the vibratory actions of the piezoelectric transducer 57. When the transducer 57 is actuated, the contact points 50 and 52 alternatingly contacts the tooth and then moves away from the tooth, as shown in the dashed outlines of FIG. 5B FIG. 6A shows another cantilevered appliance with a custom conformal base 36 that mounts the appliance to teeth 10A-10C which in turn supports assemblies 67 and 68. The assembly 67 drives an arm 66 in contact with a fixed point 69 at one tooth 10C. In this embodiment, an arm 62 extends from the arm 66 at point 64 and is driven by a piezoelectric device (not shown). The arm 62 is counterbalanced by a pendulum weight or mass 60. The pieozoelectric actuator moves the mass 60 and such motion causes the arm 66 to vibrate the tooth. FIG. 6B shows in more detail the pendulum swing of the mass 60. The movement of the mass 60 transmits sound to the user through the fixed point 69.

Figure 7A:
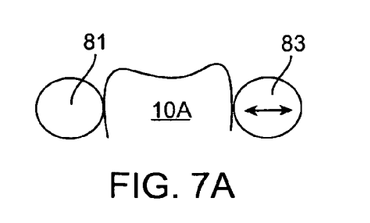
FIGS. 7A-7B show exemplary operations of a bone conduction dental appliance.
Figure 7B:
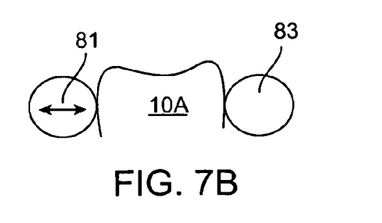

FIGS. 7A-7B shows an exemplary view of the bone conduction operation. In these figures, tooth 10A is clamped by the appliance's assemblies 81 and 83. One, but not both, of the assemblies 81 or 83 preferably moves in a horizontal direction against the tooth 10A to deliver vibratory energy that is then converted into sound through bone conduction.

Figure 8A:
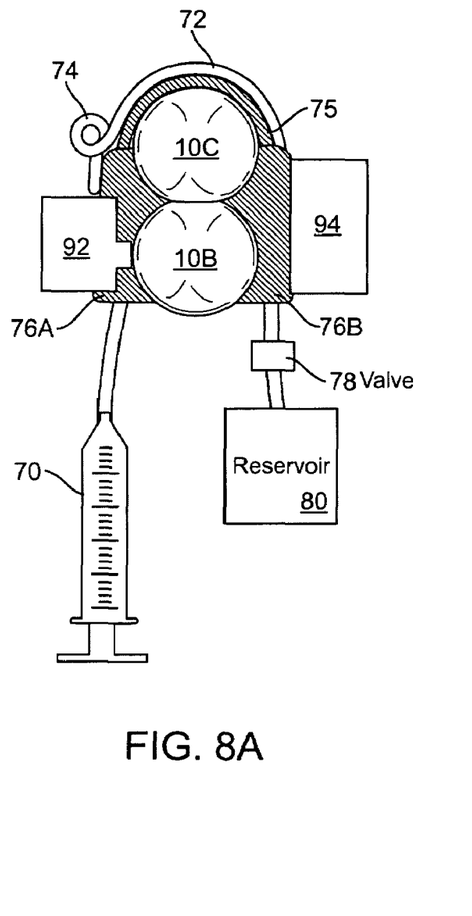
FIGS. 8A-8B show exemplary custom dental appliance embodiments fabricated with a hardenable material.
Figure 8B:
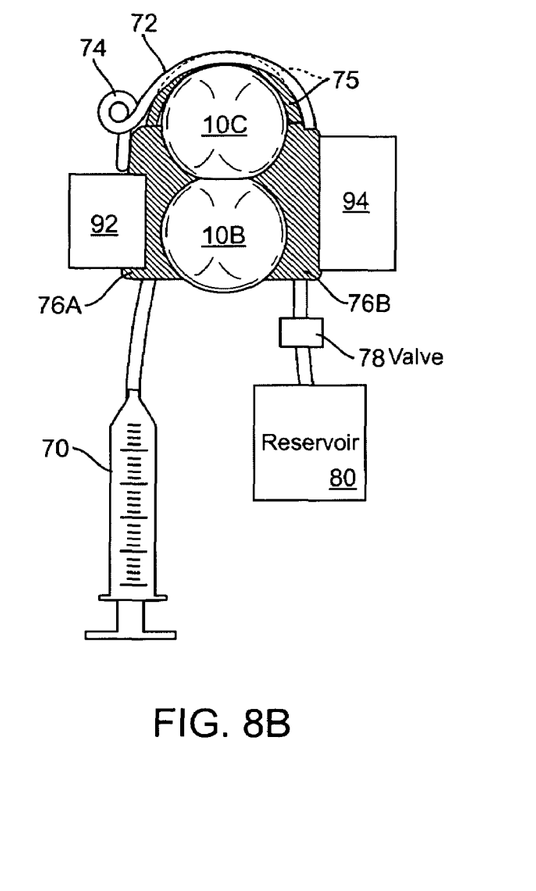

FIG. 8A shows another embodiment of a custom fitted intraoral appliance. In the embodiment of FIG. 8A, an assembly 92 directly contacts the tooth 10A, while in FIG. 8B, the contact is done at the back of tooth 10C. When actuated by assembly 92, sound energy is transmitted or conducted through tooth 10B at the contact point. In FIG. 8A, a conformal base 76 includes first and second portions 76A and 76B that are interconnected by a path or channel 75. In FIG. 8B, a cantilevered arm 72 physically connects assemblies 92-94 and also makes bone conduction contact at the back of the tooth 10C. When actuated by assembly 92, sound energy is transmitted through the arm 72 and sound is conducted through tooth 10C. The conformal base 76 receives an injection of a hardenable hydrogel or polymer through a syringe 70. The material flows into portion 76A, channel 75 and then to portion 76B. A pressure relief value 78 is positioned at the exit of portion 76B so that if the composition overfills the conformal base 76, excess materials are vented into a reservoir 80 for suitable disposal. Alternatively, the hardenable material can be used to conform to the user's dentition while providing coupling force to the actuator to make contact with the tooth.

As mentioned above, the hardenable dental compositions can be any suitable materials known to one skilled in the art. For example, U.S. Pat. No. 7,361,216 discloses ionomer compositions containing nanofillers. The compositions can be used in a variety of dental and orthodontic applications, for example, as adhesives, cements, restoratives, coatings and sealants. The material optionally includes a polymerizable component. The polymerizable component can optionally be an ethylenically unsaturated compound with or without acid functionality. The polymerizable component can be part of a hardenable resin. These resins are generally thermosetting materials capable of being hardened to form a polymer network including, for example, acrylate-functional materials, methacrylate-functional materials, epoxy-functional materials, vinyl-functional materials, and mixtures thereof. Typically, the hardenable resin is made from one or more matrix-forming oligomer, monomer, polymer, or blend thereof. In certain embodiments where the dental composition can be a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies, and mixtures and derivatives thereof. One class of hardenable materials includes materials having polymerizable components with free radically active functional groups. Examples of such materials include monomers having one or more ethylenically unsaturated groups, oligomers having one or more ethylenically unsaturated groups, polymers having one or more ethylenically unsaturated groups, and combinations thereof.

Figure 8C:
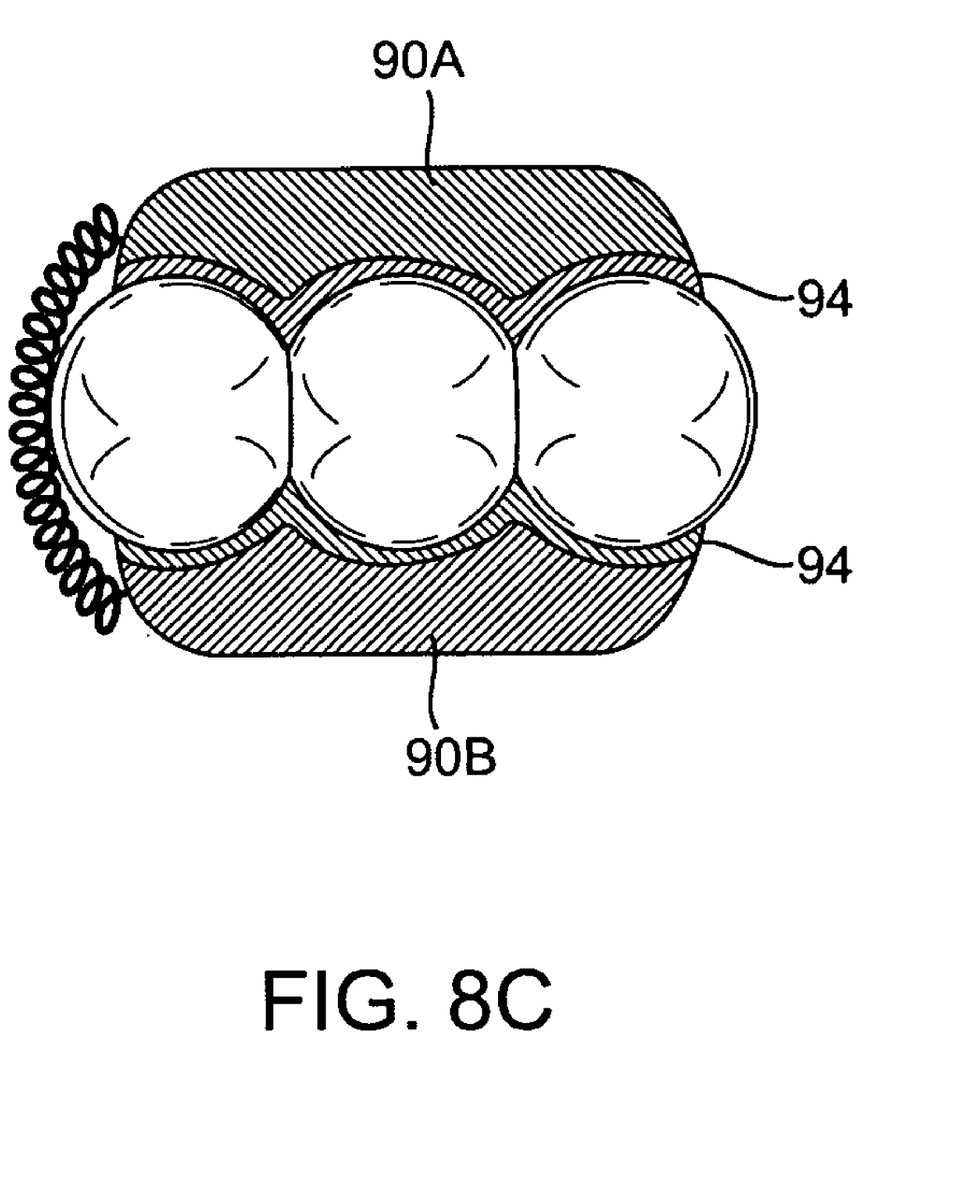
FIG. 8C shows another custom dental appliance with a fillable pocket to conform to a tooth at first use.

FIG. 8C shows one embodiment with a base in the form of a clam shell that has a cavity in the regions that contact the teeth that can be filled with PVS or other types of impression materials at the time of first use to conform to the patients dentition.

In FIG. 8C, a custom fit base has two portions 90A and 90B. The portions 90A and 90B in turn have one or more cavities 94 positioned in one or more tooth contacting regions 94. At first use, the cavities 94 are then filled with PVS or an impression material such as the material discussed above to conform to the patient's dentition. When they harden, the result is a customized fit to the patient's dentition.

In order to transmit the vibrations corresponding to the received auditory signals efficiently and with minimal loss to the tooth or teeth, secure mechanical contact between the actuator and the tooth is ideally maintained to ensure efficient vibratory communication. Accordingly, any number of mechanisms may be utilized to maintain this vibratory communication.

For any of the variations described above, they may be utilized as a single device or in combination with any other variation herein, as practicable, to achieve the desired hearing level in the user. Moreover, more than one oral appliance device and electronics and/or actuator assemblies may be utilized at any one time. For example, multiple actuator assemblies may be placed on multiple dental implants. Although they are typically mounted on the upper row of teeth, multiple assemblies may alternatively be positioned and located along the lower row of teeth or both rows as well. Moreover, each of the assemblies may be configured to transmit vibrations within a uniform frequency range. Alternatively in other variations, different assemblies may be configured to vibrate within non-overlapping frequency ranges between each assembly. As mentioned above, each actuator can be programmed or preset for a different frequency response such that each actuator may be optimized for a different frequency response and/or transmission to deliver a relatively high-fidelity sound to the user.

Moreover, each of the different actuators can also be programmed to vibrate in a manner which indicates the directionality of sound received by the microphone worn by the user. For example, different actuators positioned at different locations within the user's mouth can vibrate in a specified manner by providing sound or vibrational queues to inform the user which direction a sound was detected relative to an orientation of the user. For instance, a first actuator located, e.g., on a user's left tooth, can be programmed to vibrate for sound detected originating from the user's left side. Similarly, a second actuator located, e.g., on a user's right tooth, can be programmed to vibrate for sound detected originating from the user's right side. Other variations and queues may be utilized as these examples are intended to be illustrative of potential variations.

Figure 9:
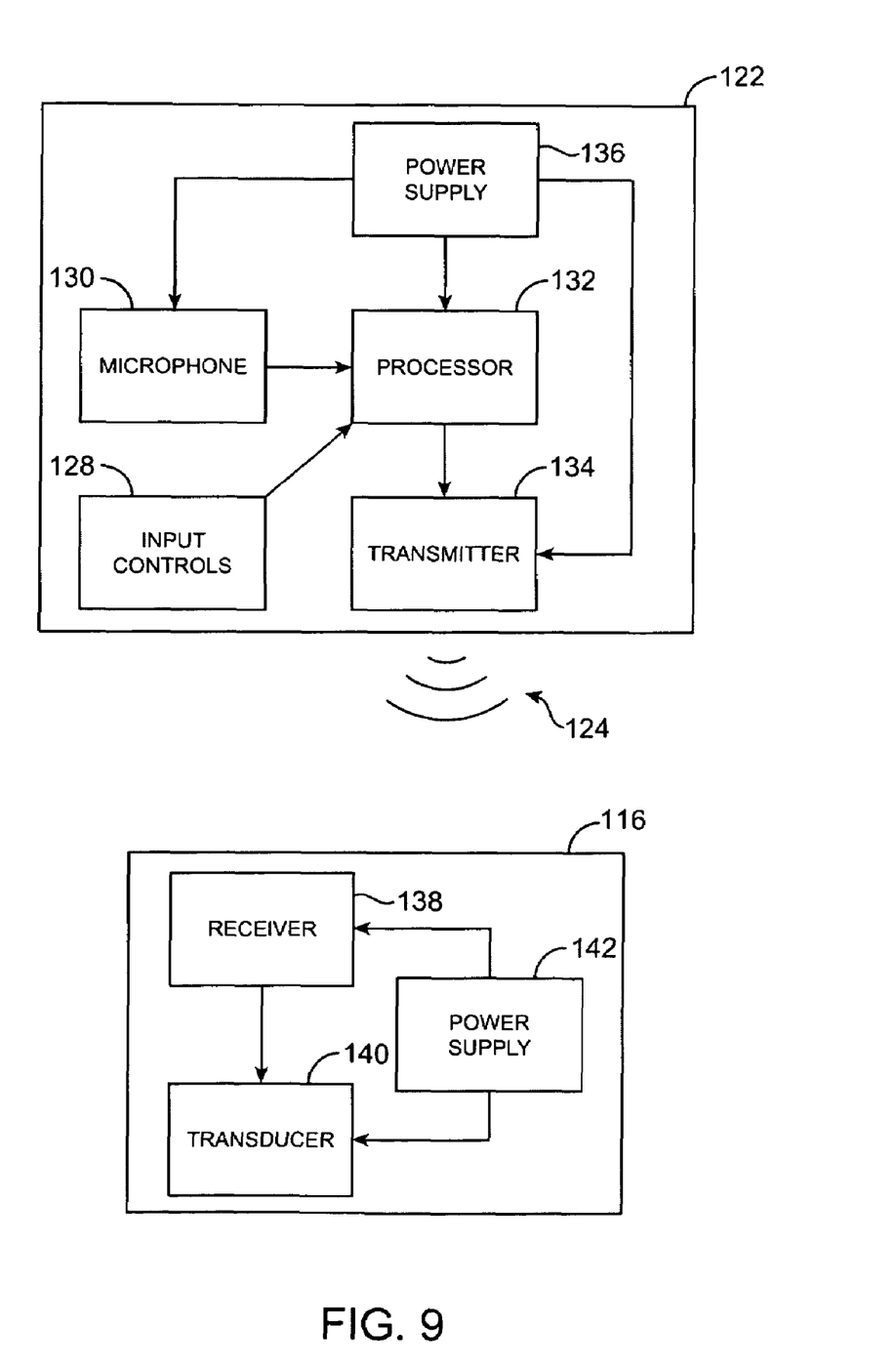
FIG. 9 shows an illustrative configuration of the individual components in a variation of the oral appliance device having an external transmitting assembly with a receiving and transducer assembly within the mouth.

FIG. 9 illustrates a schematic representation of one variation of hearing aid assembly 114 utilizing an extra-buccal transmitter assembly 122, which may generally comprise microphone 130 for receiving sounds and which is electrically connected to processor 132 for processing the auditory signals. Processor 132 may be connected electrically to transmitter 134 for transmitting the processed signals to the electronics and/or actuator assembly 116 disposed upon or adjacent to the user's teeth. The microphone 130 and processor 132 may be configured to detect and process auditory signals in any practicable range, but may be configured in one variation to detect auditory signals ranging from, e.g., 250 Hertz to 20,000 Hertz.

With respect to microphone 130, a variety of various microphone systems may be utilized. For instance, microphone 130 may be a digital, analog, and/or directional type microphone. Such various types of microphones may be interchangeably configured to be utilized with the assembly, if so desired.

Power supply 136 may be connected to each of the components in transmitter assembly 122 to provide power thereto. The transmitter signals 124 may be in any wireless form utilizing, e.g., radio frequency, ultrasound, microwave, Blue Tooth®, etc. for transmission to assembly 116. Assembly 122 may also optionally include one or more input controls 128 that a user may manipulate to adjust various acoustic parameters of the electronics and/or actuator assembly 116, such as acoustic focusing, volume control, filtration, muting, frequency optimization, sound adjustments, and tone adjustments, etc.

The signals transmitted 124 by transmitter 134 may be received by electronics and/or actuator assembly 116 via receiver 138, which may be connected to an internal processor for additional processing of the received signals. The received signals may be communicated to actuator 140, which may vibrate the tooth to conduct the vibratory signals through the tooth and bone and subsequently to the middle ear to facilitate hearing of the user. Actuator 140 may be configured as any number of different vibratory mechanisms. For instance, in one variation, actuator 140 may be an electromagnetically actuated actuator. In other variations, actuator 140 may be in the form of a piezoelectric crystal having a range of vibratory frequencies, e.g., between 250 to 4000 Hz.

Power supply 142 may also be included with assembly 116 to provide power to the receiver, actuator, and/or processor, if also included. Although power supply 142 may be a simple battery, replaceable or permanent, other variations may include a power supply 142 which is charged by inductance via an external charger. Additionally, power supply 142 may alternatively be charged via direct coupling to an alternating current (AC) or direct current (DC) source. Other variations may include a power supply 142 which is charged via a mechanical mechanism, such as an internal pendulum or slidable electrical inductance charger as known in the art, which is actuated via, e.g., motions of the jaw and/or movement for translating the mechanical motion into stored electrical energy for charging power supply 142.

Figure 10:
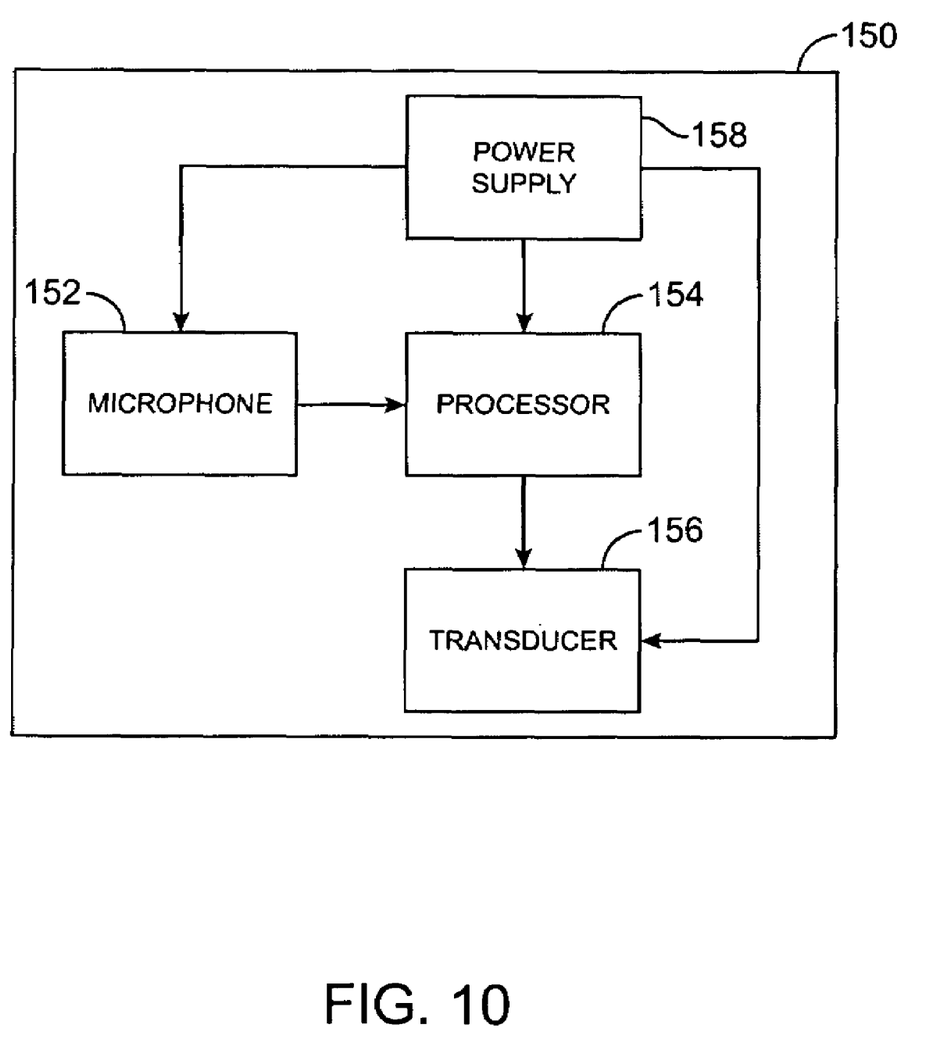
FIG. 10 shows an illustrative configuration of another variation of the device in which the entire assembly is contained by the oral appliance within the user's mouth.

In another variation of assembly 116, rather than utilizing an extra-buccal transmitter, hearing aid assembly 150 may be configured as an independent assembly contained entirely within the user's mouth, as shown in FIG. 4. Accordingly, assembly 150 may include an internal microphone 152 in communication with an on-board processor 154. Internal microphone 152 may comprise any number of different types of microphones, as described above. Processor 154 may be used to process any received auditory signals for filtering and/or amplifying the signals and transmitting them to actuator 156, which is in vibratory contact against the tooth surface. Power supply 158, as described above, may also be included within assembly 50 for providing power to each of the components of assembly 150 as necessary.

In order to transmit the vibrations corresponding to the received auditory signals efficiently and with minimal loss to the tooth or teeth, secure mechanical contact between the actuator and the tooth is ideally maintained to ensure efficient vibratory communication. Accordingly, any number of mechanisms may be utilized to maintain this vibratory communication.

In variations where the one or more microphones are positioned in intra-buccal locations, the microphone may be integrated directly into the electronics and/or actuator assembly, as described above. However, in additional variation, the microphone unit may be positioned at a distance from the actuator assemblies to minimize feedback. In one example, the microphone unit may be separated from electronics and/or actuator assembly.

The vibratory actuator may generally include a microphone for receiving sounds and which is electrically connected to a processor for processing the auditory signals. The processor may be electrically connected to an antenna for receiving wireless communication signals, e.g., input control signals from an external remote control and/or other external sound generating devices, e.g., cell phones, telephones, stereos, MP3 players, and other media players. The microphone and processor may be configured to detect and process auditory signals in any practicable range, but may be configured in one variation to detect auditory signals ranging from, e.g., 250 Hertz to 20,000 Hertz. The detected and processed signals may be amplified via amplifier, which increases the output levels for vibrational transmission by actuator into the adjacent, or otherwise coupled, bone structure such as a patient's tooth or teeth.

With respect to the microphone, a variety of various microphone systems may be utilized. For instance, the microphone may be a digital, analog, piezoelectric, and/or directional type microphone. Such various types of microphones may be interchangeably configured to be utilized with the assembly, if so desired.

The signals transmitted may be received by electronics and/or actuator assembly via a receiver, which may be connected to an internal processor for additional processing of the received signals. The received signals may be communicated to the actuator, which may vibrate the tooth to conduct the vibratory signals through the tooth and bone and subsequently to the middle ear to facilitate hearing of the user. The actuator may be configured as any number of different vibratory mechanisms. For instance, in one variation, the actuator may be an electromagnetically actuated actuator. In other variations, the actuator may be in the form of a piezoelectric crystal having a range of vibratory frequencies, e.g., between 250 to 20,000 Hz.

The dental appliance can be used to treat hearing loss, tinnitus or stuttering. For stuttering, the implant can play frequency shifted and delayed version of the sound directed at the patient and this delayed playback stops the patient's stuttering. For example, the sound is frequency shifted by about 500 Hz and the auditory feedback can be delayed by about 60 ms. The self-contained dental implant assists those who stutter. With the device in place, stuttering is reduced and speech produced is judged to be more natural than without the device.

The implant can treat tinnitus, which is a condition in which sound is perceived in one or both ears or in the head when no external sound is present. Such a condition may typically be treated by masking the tinnitus via a generated noise or sound. In one variation, the frequency or frequencies of the tinnitus may be determined through an audiology examination to pinpoint the range(s) in which the tinnitus occurs in the patient. This frequency or frequencies may then be programmed into a removable oral device which is configured to generate sounds which are conducted via the user's tooth or bones to mask the tinnitus. One method for treating tinnitus may generally comprise masking the tinnitus where at least one frequency of sound (e.g., any tone, music, or treatment using a wide-band or narrow-band noise) is generated via an actuatable actuator positioned against at least one tooth such that the sound is transmitted via vibratory conductance to an inner ear of the patient, whereby the sound completely or at least partially masks the tinnitus perceived by the patient. In generating a wide-band noise, the sound level may be raised to be at or above the tinnitus level to mask not only the perceived tinnitus but also other sounds. Alternatively, in generating a narrow-band noise, the sound level may be narrowed to the specific frequency of the tinnitus such that only the perceived tinnitus is masked and other frequencies of sound may still be perceived by the user. Another method may treat the patient by habituating the patient to their tinnitus where the actuatable actuator may be vibrated within a wide-band or narrow-band noise targeted to the tinnitus frequency perceived by the patient overlayed upon a wide-frequency spectrum sound. This wide-frequency spectrum sound, e.g., music, may extend over a range which allows the patient to periodically hear their tinnitus through the sound and thus defocus their attention to the tinnitus. In enhancing the treatment for tinnitus, a technician, audiologist, physician, etc., may first determine the one or more frequencies of tinnitus perceived by the patient. Once the one or more frequencies have been determined, the audiologist or physician may determine the type of treatment to be implemented, e.g., masking or habituation. Then this information may be utilized to develop the appropriate treatment and to compile the electronic treatment program file which may be transmitted, e.g., wirelessly, to a processor coupled to the actuatable actuator such that the actuator is programmed to vibrate in accordance with the treatment program.

In use, an implant containing the actuator may be placed against one or more teeth of the patient and the actuator may be actuated by the user when tinnitus is perceived to generate the one or more frequencies against the tooth or teeth. The generated vibration may be transmitted via vibratory conductance through the tooth or teeth and to the inner ear of the patient such that each of the frequencies of the perceived tinnitus is masked completely or at least partially. The oral implant may be programmed with a tinnitus treatment algorithm which utilizes the one or more frequencies for treatment. This tinnitus treatment algorithm may be uploaded to the oral appliance wirelessly by an external programming device to enable the actuator to vibrate according to the algorithm for treating the tinnitus. Moreover, the oral appliance may be used alone for treating tinnitus or in combination with one or more hearing aid devices for treating patients who suffer not only from tinnitus but also from hearing loss.

Although the foregoing discloses a user formable appliance with EVA or gels that can be hardened by the user, mass customization techniques can be used to enable the user to fabricate his or her own appliance at home or at a shared facility such as a copying facility (Kinko's), for example. For example, in one exemplary embodiment to fabricate an oral appliance, the system first fabricates a scaffold of an oral appliance using a rapid prototyping system that the user can own, rent, or otherwise have access to. One such rapid prototyping machine is called Fused Deposition Modeling (FDM). The scaffold is subsequently immersed into a resin to strengthen the scaffold. Excess resin and support material is then trimmed from the scaffold to arrive at a finished device.

FDM is one way to generate the oral appliance. In FDM, a plastic filament is unwound from a coil and supplies material to an extrusion nozzle. The nozzle is heated to melt the plastic and has a mechanism which allows the flow of the melted plastic to be controlled. The nozzle is mounted to a mechanical stage which can be moved three-dimensionally. As the nozzle is moved over the required geometry, it deposits a thin bead of extruded plastic to form each layer. The plastic hardens immediately after being squirted from the nozzle and bonds to the layer below. The entire system is contained within an oven chamber which is held at a temperature just below the melting point of the plastic. Thus, only a small amount of additional thermal energy needs to be supplied by the extrusion nozzle to cause the plastic to melt. This provides much better control of the process. Several materials are available for the process including a nylon-like polymer and both machinable and investment casting waxes. ABS plastic material can be used to provide high layer to layer bonding. Water-soluble support materials can be used and subsequently removed simply by washing them away. FDM machines are available from Stratasys, among others.

In another embodiment, Selective Laser Sintering (SLS) can be used. The process is similar to the SLA process. In SLS, a laser beam is traced over the surface of a tightly compacted powder made of thermoplastic material. The powder is spread by a roller over the surface of a build cylinder. A piston moves down one object layer thickness to accommodate the layer of powder. The piston moves upward incrementally to supply powder for the process. Heat from the laser melts the powder where it strikes under guidance of the scanner system. The laser used provides a concentrated infrared heating beam. The entire fabrication chamber is sealed and maintained at a temperature just below the melting point of the plastic powder. Thus, heat from the laser need only elevate the temperature slightly to cause sintering, greatly speeding the process. After the object is fully formed, the piston is raised to elevate the object. Excess powder is simply brushed away and final manual finishing may be carried out.

In yet another embodiment, a 3D printer using inkjet head can be used. In this embodiment, the method is very reminiscent of selective laser sintering, except that the laser is replaced by an inkjet head. The multi-channel jetting head deposits a liquid adhesive compound onto the top layer of a bed of powder object material. The particles of the powder become bonded in the areas where the adhesive is deposited. Once a layer is completed the piston moves down by the thickness of a layer. As in selective laser sintering, the powder supply system (E) is similar in function to the build cylinder In this case the piston moves upward incrementally to supply powder for the process and the roller (D) spreads and compresses the powder on the top of the build cylinder. The process is repeated until the entire object is completed within the powder bed. Exemplary machines are available from Z Corp. which uses the process to create models out of starch, plaster and other types of powders.

In other embodiment, Thermal Phase Change inkjets can be used for ballistic particle manufacturing (BPM). The phase change inkjet technologies rely on squirting a build material in a liquid or melted state which cools or otherwise hardens to form a solid on impact. Exemplary systems from 3D Systems include the ThermoJet Modeler which utilizes several hundred nozzles. In a Solidscape machine uses plastic object and wax and support materials which are held in a melted liquid state at elevated temperature in reservoirs. The liquids are fed to individual jetting heads through thermally insulated tubing. The jetting heads squirt tiny droplets of the materials as they are moved side to side in the required geometry to form the layer of the object. The heads are controlled and only place droplets where they are required to. The materials harden by rapidly dropping in temperature as they are deposited. After an entire layer of the object is formed by jetting, a milling head is passed over the layer to make it a uniform thickness. Particles are vacuumed away as the milling head cuts and are captured in a filter. After the object is completed, the wax support material is either melted or dissolved away.

Another process called Photopolymer Phase Change Inkjets process is based on photopolymers, but uses a wide area inkjet head to layerwise deposit both build and support materials. It subsequently completely cures each layer after it is deposited with a UV flood lamp mounted on the printhead. The support material, which is also a photopolymer, is removed by washing it away with pressurized water in a secondary operation.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. An intraoral apparatus, comprising:
an actuatable transducer configured to transmit sound through bone conduction;
a user-fabricated custom fit base having a first and a second housing configured to be securely pressed against sides of one or more teeth on opposite surfaces of the one or more teeth or oral tissue, respectively, wherein the actuatable transducer is disposed within or upon the first housing and is configured to transmit vibrations to the one or more teeth; and
an arm coupled to the first and second housings.

2. The apparatus of claim 1 wherein the user fabricated custom fit base comprises a thermoplastic co-polymer.

3. The apparatus of claim 1, wherein the user fabricated custom fit base comprises ethylene vinyl acetate (EVA) or polyethylene material.

4. The apparatus of claim 1, wherein the user fabricated custom fit base comprises a hardenable material.

5. The apparatus of claim 4, further comprising a relief valve in fluid communication with the custom fit base to discharge excess hardenable material.

6. The apparatus of claim 1, wherein the custom fit base comprises one or more cavities in one or more tooth contacting regions.

7. The apparatus of claim 6, wherein the one or more cavities are filled with PVS or an impression material at first use to conform to the patient's dentition.

8. The apparatus of claim 1, wherein the arm comprises a loop.

9. The apparatus of claim 1, wherein the arm is corrugated, jagged, round, or rectangular.

10. The apparatus of claim 1, wherein the arm contacts the one or more teeth to deliver sound energy.

11. The apparatus of claim 1, wherein the custom fit base slidably cooperates with the arm to fit different tooth sizes.

12. The apparatus of claim 1, wherein the first housing comprises a moveable dental contact point which allows a user to adjust a contact position with the one or more teeth.

13. The apparatus of claim 1 further comprising an electronic assembly disposed within or upon the first housing.

14. The apparatus of claim 13 wherein the electronic assembly further comprises a receiver in wireless communication with an externally located transmitter assembly.

15. The apparatus of claim 13 wherein the electronic assembly is encapsulated within the first or second housing.

16. The apparatus of claim 13 wherein the electronic assembly further comprises a power supply in electrical communication with the transducer.

17. The apparatus of claim 13 wherein the electronic assembly further comprises a processor in electrical communication with the transducer.

18. The apparatus of claim 13 wherein the electronic assembly further comprises a microphone for receiving auditory signals and which is in electrical communication with the processor.

19. A method of transmitting, vibrations, comprising:
heating a base material;
biting into the base material to form a custom-fit base wherein the custom-fit base having a first and a second housing is configured to be securely pressed against sides of one or more teeth on opposite surfaces of the one or more teeth or oral tissue, respectively, the custom-fit base further having an arm coupled to the first and second housings;
positioning an actuatable transducer on or along the first housing of the base;
securing the custom-fit base and the actuatable transducer on the one or more teeth or oral tissue such that the transducer and the one or more teeth are in vibrational communication; and
actuating the transducer such that an audio signal is vibrationally conducted through the one or more teeth or oral tissue.

* * * * *